ized Transduction System", *BioEssays* 13(3):127–134 (1991).
United States Patent [19]
Fishman et al.

[11] Patent Number: 5,543,498
[45] Date of Patent: Aug. 6, 1996

[54] PEPTIDES TO OVERCOME INHIBITION OF NERVE GROWTH

[75] Inventors: Mark C. Fishman, Newton Centre, Mass.; Michihiro Igarashi, Saitama, Japan; Stephen M. Strittmatter, Clinton, Conn.

[73] Assignee: The General Hospital Corporation, Boston, Mass.

[21] Appl. No.: 417,279

[22] Filed: Apr. 5, 1995

Related U.S. Application Data

[63] Continuation of Ser. No. 166,350, Dec. 14, 1993, abandoned, which is a continuation-in-part of Ser. No. 162,480, Dec. 7, 1993, abandoned.

[51] Int. Cl.$^6$ .......................... A61K 38/00; A61K 38/04; C07K 7/06
[52] U.S. Cl. ............................................................ 530/328
[58] Field of Search ........................... 514/2, 15; 530/328

[56] References Cited

FOREIGN PATENT DOCUMENTS

WO92/18138 10/1992 WIPO.
WO93/06851 4/1993 WIPO.

OTHER PUBLICATIONS

Strittmatter et al., "An amino-terminal domain of the growth-associated protein GAP-43 mediates its effects on filopodial formation and cell spreading," *J. Cell Sci.* 107:195–204 (1994).
Strittmatter et al., "GAP-43 as a Plasticity Protein in Neuronal Form and Repair," *J. Neurobiol.* 23(5):507–520 (1992).
Benowitz et al., "A Membrane Phosphoprotein Associated With Neural Development, Axonal Regeneration, Phospholipid Metabolism, and Synaptic Plasticity", *TINS* 10(12):527–532 (1987).
Caroni et al., "Two Membrane Protein Fractions from Rat Central Myelin with Inhibitory Properties for Neurite Growth and Fibroblast Spreading", *J. Cell Biol.* 106:1281–1288 (1988).
David et al., "Axonal Elongation into Peripheral Nervous System 'Bridges' After Central Nervous System Injury in Adult Rats", *Science* 214(20):931–933 (1981).
Igarashi et al., "Mediation by G Proteins of Signals That Cause Collapse of Growth Cones", *Science* 259:77–79 (1993).
Keynes et al., "Repellent Cues in Axon Guidance", *Cur. Opin. Neurobiol.* 2:55–59 (1992).
Raper et al., "The Enrichment of a Neuronal Growth Cone Collapsing Activity from Embryonic Chick Brain", *Neuron* 2:21–29 (1990).
Schwab et al., "Inhibitors of Neurite Growth", *Ann. Rev. Neurosci.* 16:565–595 (1993).
Skene, J. H. P., "Axonal Growth-Associated Proteins", *Ann. Rev. Neurosci.* 12:127–156 (1989).
Strittmatter et al., "The Neuronal Growth Cone as a Specialized Transduction System", *BioEssays* 13(3):127–134 (1991).
Strittmatter et al., "GAP-43 Augments G. Protein-Coupled Receptor Transduction in *Xenopus laevis* Oocytes", *Proc. Natl. Acad. Sci. USA* 90:5327–5331 (1993).
Strittmater et al., "$G_0$ is a Major Growth Cone Protein Subject to Regulation by GAP-43", *Nature* 344:836–841 (1990).
Strittmatter et al., "An Intracellular Guanine Nucleotide Release Protein for $G_0$", *J. Biol. Chem.* 266(30):22465–22471 (1991).
Sudo et al., "Palmitoylation Alters Protein Activity: Blockade of $G_0$ Stimulation by GAP-43", *Embo J.* 11(6):2095–2102 (1992).
Louglin et al(eds), *Neurotrophic Factors* (AP 1993) pp. 235–237, 241, 265–267.
Zuber et al Nature 341 345–8 (1989).
Florio et al JBC 264 3909–15 (1989).
Alexander et al J. Immunol 150 1–7 (1993).
Zuber, et al., *A Membrane Targeting Signal in the Amino Terminns of the Neuronal Protein GAP–43*, Nature, 341 345–348 (1989).
Florio, et al., *Mechanisms of Muscariaic Receptor Action of $G_0$ Reconstituted Phospholipid Vesicles*, J. Biol. Chem, 264 3909–3915 (1989).
Alexander et al., *Functional Consequences of Engagement of the T Cell Receptor by Low Affinity Lipands.*, J. Immunol., 150 1–7 (1993).

Primary Examiner—Garnette D. Draper
Assistant Examiner—Stephen Gucker
Attorney, Agent, or Firm—Sterne, Kessler, Goldstein & Fox P.L.L.C.

[57] ABSTRACT

Inhibition of nerve growth normally helps to prevent aberrant pathway or target selection, but also prevents needed regeneration in the mammalian central nervous system. The responsible inhibitory ligands are unknown, but pertussis toxin-sensitive G proteins, which are enriched in growth cones, appear to be involved in causing the responding growth cones to collapse. GAP-43 is an intracellular protein that can amplify the response to the stimulation of G protein-coupled receptors. We have attempted to modify the sensitivity of nerves to inhibitory signals by the use of GAP-43 peptides. The peptide corresponding to the native amino terminus sequence stimulates $G_o$ and enhances the growth cone collapse induced by inhibitory ligands. Modification of two critical cysteines generates peptides which inhibit $G_o$ and which markedly reduce the degree of inhibitor-mediated growth cone collapse.

4 Claims, 5 Drawing Sheets

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:

(A) LENGTH: 10 amino acids
(B) TYPE: amino acid
(D) TOPOLOGY: both (xi) SEQUENCE DESCRIPTION: SEQ ID NO:1:

Met Leu Cys Cys Met Arg Arg Thr Lys Gln
1               5                   10

(2) INFORMATION FOR SEQ ID NO:2:

(i) SEQUENCE CHARACTERISTICS:
(A) LENGTH: 10 amino acids
(B) TYPE: amino acid
(D) TOPOLOGY: both (xi) SEQUENCE DESCRIPTION: SEQ ID NO:2:

Met Leu Met Met Met Arg Arg Thr Lys Gln
1               5                   10

(2) INFORMATION FOR SEQ ID NO:3:

(i) SEQUENCE CHARACTERISTICS:
(A) LENGTH: 10 amino acids
(B) TYPE: amino acid
(D) TOPOLOGY: both (xi) SEQUENCE DESCRIPTION: SEQ ID NO:3:

Met Leu Tyr Tyr Met Arg Arg Thr Lys Gln
1               5                   10

(2) INFORMATION FOR SEQ ID NO:4:

(i) SEQUENCE CHARACTERISTICS:
(A) LENGTH: 10 amino acids
(B) TYPE: amino acid
(D) TOPOLOGY: both (xi) SEQUENCE DESCRIPTION: SEQ ID NO:4:

Met Leu Asp Asp Met Arg Arg Thr Lys Gln
1               5                   10

(2) INFORMATION FOR SEQ ID NO:5:

(i) SEQUENCE CHARACTERISTICS:
(A) LENGTH: 10 amino acids
(B) TYPE: amino acid
(D) TOPOLOGY: both (xi) SEQUENCE DESCRIPTION: SEQ ID NO:5:

Met Leu Glu Glu Met Arg Arg Thr Lys Gln
1               5                   10

(2) INFORMATION FOR SEQ ID NO:6:

(i) SEQUENCE CHARACTERISTICS:
(A) LENGTH: 10 amino acids
(B) TYPE: amino acid
(D) TOPOLOGY: both (xi) SEQUENCE DESCRIPTION: SEQ ID NO:6:

Met Leu Lys Lys Met Arg Arg Thr Lys Gln
1               5                   10

(2) INFORMATION FOR SEQ ID NO:7:

(i) SEQUENCE CHARACTERISTICS:
(A) LENGTH: 10 amino acids
(B) TYPE: amino acid ( D ) TOPOLOGY: both ( x i ) SEQUENCE DESCRIPTION: SEQ ID NO:7:

Met Leu Arg Arg Met Arg Arg Thr Lys Gln
1               5                   10

( 2 ) INFORMATION FOR SEQ ID NO:8:

( i ) SEQUENCE CHARACTERISTICS:
( A ) LENGTH: 10 amino acids
( B ) TYPE: amino acid
( D ) TOPOLOGY: both ( x i ) SEQUENCE DESCRIPTION: SEQ ID NO:8:

Met Leu Ser Ser Met Arg Arg Thr Lys Gln
1               5                   10

( 2 ) INFORMATION FOR SEQ ID NO:9:

( i ) SEQUENCE CHARACTERISTICS:
( A ) LENGTH: 10 amino acids
( B ) TYPE: amino acid
( D ) TOPOLOGY: both ( x i ) SEQUENCE DESCRIPTION: SEQ ID NO:9:

Met Leu Trp Trp Met Arg Arg Thr Lys Gln
1               5                   10

PEPTIDES TO OVERCOME INHIBITION OF NERVE GROWTH

CROSS REFERENCE TO RELATED APPLICATION

This application is a continuation of application Ser. No. 08/166,350, filed Dec. 14, 1993, abandoned, which is a continuation-in-part of application Ser. No. 08/162,480, filed Dec. 7, 1993, abandoned. The content of all the aforesaid applications are relied upon and incorporated by reference in their entirety.

BACKGROUND OF THE INVENTION

1. Field of the Invention

The present invention relates to the field of neurology. More particularly, the invention is drawn toward the regulation of G protein functions, and the related nerve cell growth cone collapse.

2. Description of the Background Art

It has been suspected since the turn of the century, and proven more recently, that the reason injured neurons do not regenerate in the CNS is primarily because of inhibitory influences from the microenvironment, rather than from an intrinsic inability to grow (S. Ramon y Cajal, *New Ideas on the Structure of the Nervous System in Man and Vertebrate* (MIT Press, Cambridge, Mass., 1990); S. David and A. J. Agayo, *Science* 214:931 (1981); R. J. Keynes and G. M. W. Cook, *Cur. Opin. Neurobiol.* 2:55 (1992)). Included among the inhibitory influences are components of myelin and activities associated with the surfaces of brain membranes (P. Caroni and M. E. Schwab, *J. Cell Biol.* 106:1281 (1988); J. A. Raper and J. P. Kapfhammer, *Neuron* 2:21 (1990)), although their molecular identities are unknown. These factors can be assayed in vitro because they cause growth cone collapse, a feature which correlates with inhibition of nerve growth (J. A. Raper and J. P. Kapfhammer, *Neuron* 2:21 (1990); J. A. Davies et al., *Neuron* 2:11 (1990); E. C. Cox et al., *Neuron* 2:31 (1990)). The collapse of growth involves G proteins (M. Igarashi et al., *Science* 259:77 (1993)). Pertussis toxin (PTX) blocks the inhibitory influences of the aforementioned factors (M. Igarashi et al., *Science* 259:77 (1993)), but its irreversibility and toxicity significantly limits its usefulness in inhibiting growth cone collapse.

GAP-43 is a protein associated with the inner surface of growth cone membranes, and is believed to function in the regulation of nerve growth and/or nerve terminal plasticity (J. I. Benowitz and A. Routtenberg, *Trends Neurosci.* 10:527 (1987); J. H. P. Skene, *Annu. Rev. Neurosci.* 12:127 (1989); S. M. Strittmatter and M. C. Fishman, *BioEssays* 13:127 (1991)). Recently, it has been shown that GAP-43 acts as a G protein stimulator, by enhancement of guanine nucleotide exchange (S. M. Strittmatter et al., *Nature* 344:836 (1990); S. M. Strittmatter et al., *J. Biol. Chem.* 266:22465 (1991)). When injected into oocytes, GAP-43 can enhance the responsiveness to ligands for G protein-coupled receptors many-fold, suggesting that it interacts at the level of G proteins and the coupling of G proteins to receptors (S. M. Strittmatter et al., *Proc. Natl. Acad. Sci. USA* 90:5327 (1993)).

Peptides corresponding to the GAP-43 amino terminus also enhance G protein activity, suggesting that this is the active domain of GAP-43 in this interaction (S. M. Strittmatter et al., *Nature* 344:836 (1990)). Although it is not known how such peptides might enter cells, even longer peptides have been reported to enter nerve cells and affect nerve growth (E. Bloch-Gallego et al., *J. Cell Biol.* 120:485 (1993)).

SUMMARY OF THE INVENTION

The application is drawn to decapeptides capable of inhibiting nerve cell growth cone collapse.

BRIEF DESCRIPTION OF THE DRAWINGS

FIGS. 2(A) and (B) show the results of replicate experiments.

DETAILED DESCRIPTION OF THE PREFERRED EMBODIMENTS

GAP-43 has been proposed as a protein responsible for regulating a nerve's responsiveness to extracellular signals (S. M. Strittmatter et al., *Proc. Natl. Acad. Sci. USA* 90:5327 (1993)). GAP-43 directly stimulates G proteins and enhances the response of G protein-coupled receptors to their respective ligands (S. M. Strittmatter et al., *Proc. Natl. Acad. Sci. USA* 90:5327 (1993)). The GAP-43 1–10 sequence also stimulates G proteins, causes growth cone collapse, and enhances the response to inhibitory ligands.

It is not clear how these peptides enter the cell. Although the growth cone has very active uptake mechanisms, peptide exchange from within such vesicles has not been explored. However, it is known that other peptides can enter nerve cells, including mastoparan (T. Higashijima et al., *J. Biol. Chem.* 265:14176 (1990)), and an Antennapedia homeobox polypeptide of 60 amino acids, the former of which blocks (M. Igarashi et al., *Science* 259:77 (1993)) and the latter of which enhances nerve growth (S. M. Strittmatter, et al., *J. Neurosci.* 14(9):5503 (1994).

Figure 1A:
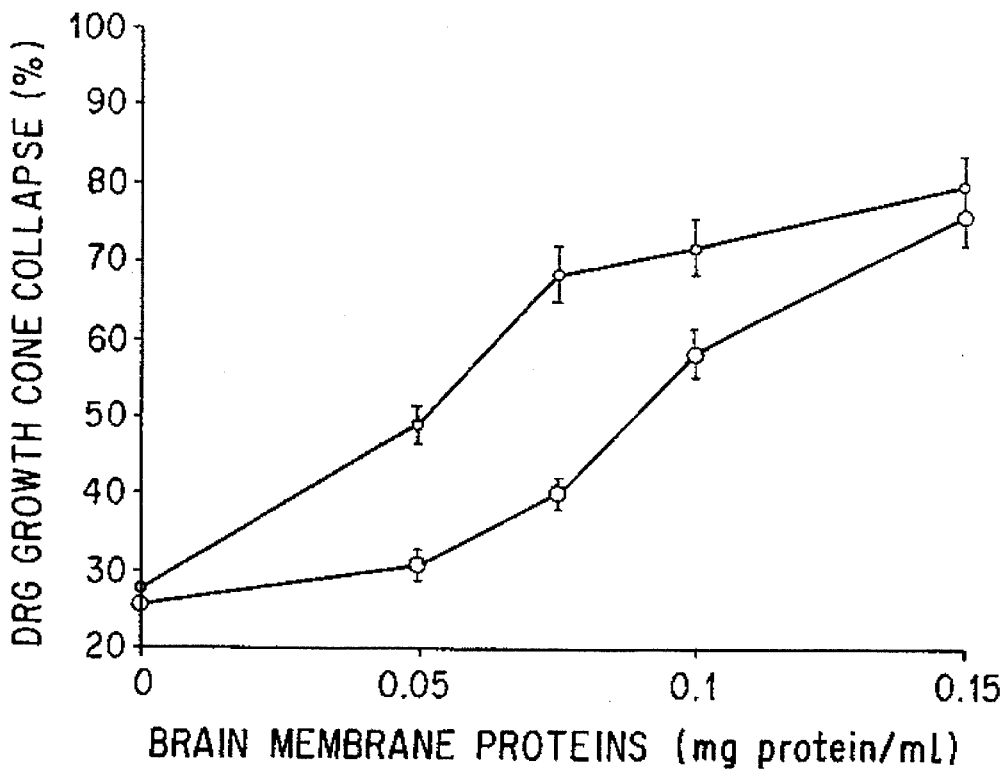
FIG. 1(A) and (B): Synergistic interaction between inhibitors of neurite outgrowth and $10^{-8}$ M of the GAP-43 1–10 N-terminus peptide (MLCCMRRTKQ) [SEQ ID NO: 1]. Growth cone collapse in response to increasing concentration of brain membrane extract (BME) prepared from chick embryos. Chick dorsal root ganglion (DRG) neurons (A) and retinal neurons (B) were cultured in the absence (open circle) and presence (closed circle) of the GAP-43 1–10 peptide. The peptide itself does not affect the proportion of collapsed growth cones, but enhances the response of both types of neurons to BME. The values shown are the means ±S.E.M. for four separate experiments.
Figure 1B:
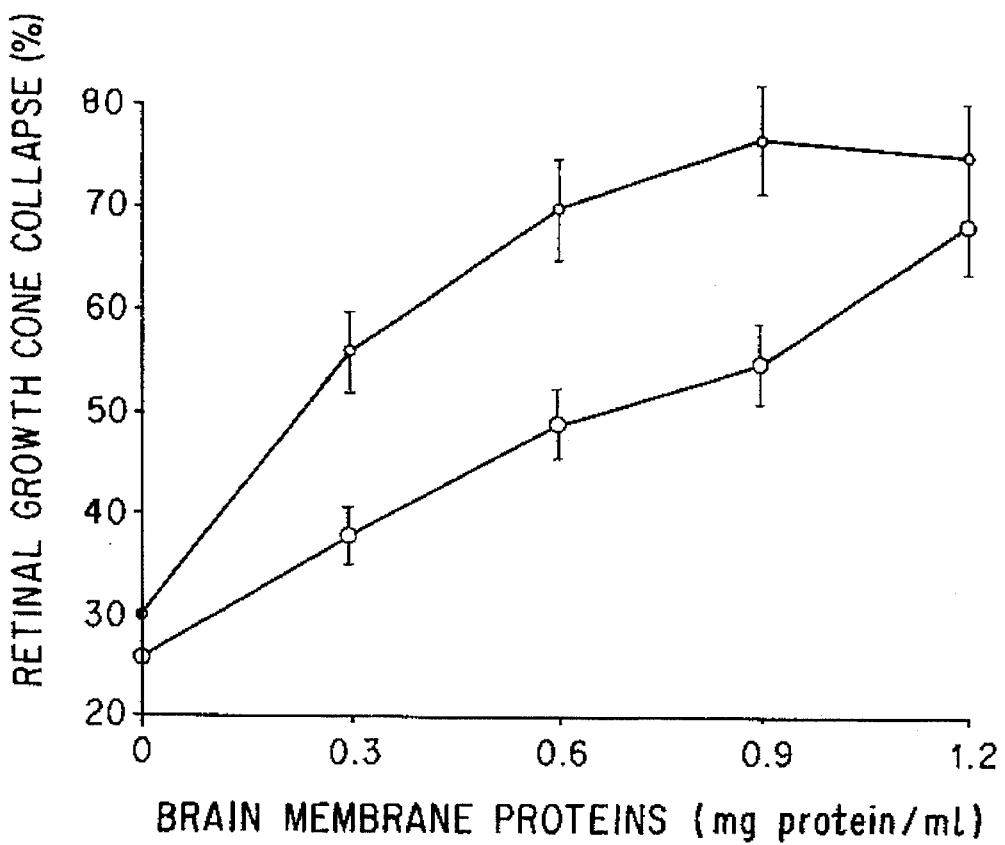
FIG. 1(C): Solubilized myelin inhibits neurite outgrowth, and is potentiated by the GAP-43 1–10 peptide. Myelin proteins of adult rat myelin (M), were solubilized by octyglucoside and dialyzed against F12 medium. Buffer (PBS) alone or the GAP-43 1–10 peptide alone does not affect the fraction of DRG neurons with neurites longer than 20 μm. The inhibitory effects of myelin (M) are potentiated by the pretreatment of neurons with $10^{-8}$M GAP-43 1–10 peptide (M+1–10). The values shown are the means ±S.E.M. for four separate experiments.
FIG. 1(D): Pretreatment with pertussis toxin (PTX) inhibits the GAP-43 1–10 peptide-induced potentiation of the effect of BME. Low concentrations of PTX (20 ng/ml; P20), which do not inhibit the collapse induced by BME, is sufficient to block the potentiation by the GAP-43 1–10 peptide. B is BME alone (protein concentration: 0.075 mg/ml); B+1–10 is BME plus the GAP-43 1–10 peptide at $10^{-8}$M; P20 is 20 ng/ml PTX, and P200 is 200 ng/ml PTX. The values shown are the means ±S.E.M. for four separate experiments.

It has been previously shown that brain membrane extracts (BME) from chick embryos cause dorsal root ganglion (DRG) and retinal growth cones to collapse in a dose-dependent manner (J. A. Raper and J. P. Kapfhammer, *Neuron* 2:21 (1990); M. Igarashi et al., *Science* 259:77 (1993)), as does the GAP-43 1–10 peptide at concentrations of 1 to 30 µM (S. M. Strittmatter, et al. *J. Neurosci* 14(9):5503 (1994)). Addition of the GAP-43 1–10 peptide at a concentration of $10^{-8}$M does not cause growth cone collapse; but does enhance the response to BME and shifts the dose response curve to the left, as shown in FIG. 1A. The collapse of retinal growth cones induced by BME was also potentiated by pretreatment with the GAP-43 1–10 peptide (FIG. 1B). Furthermore, the sensitivity of DRG neurons to BME is nearly doubled, and in the case of retinal neurons tripled, in the presence of the GAP-43 1–10 peptide.

Figure 1C:
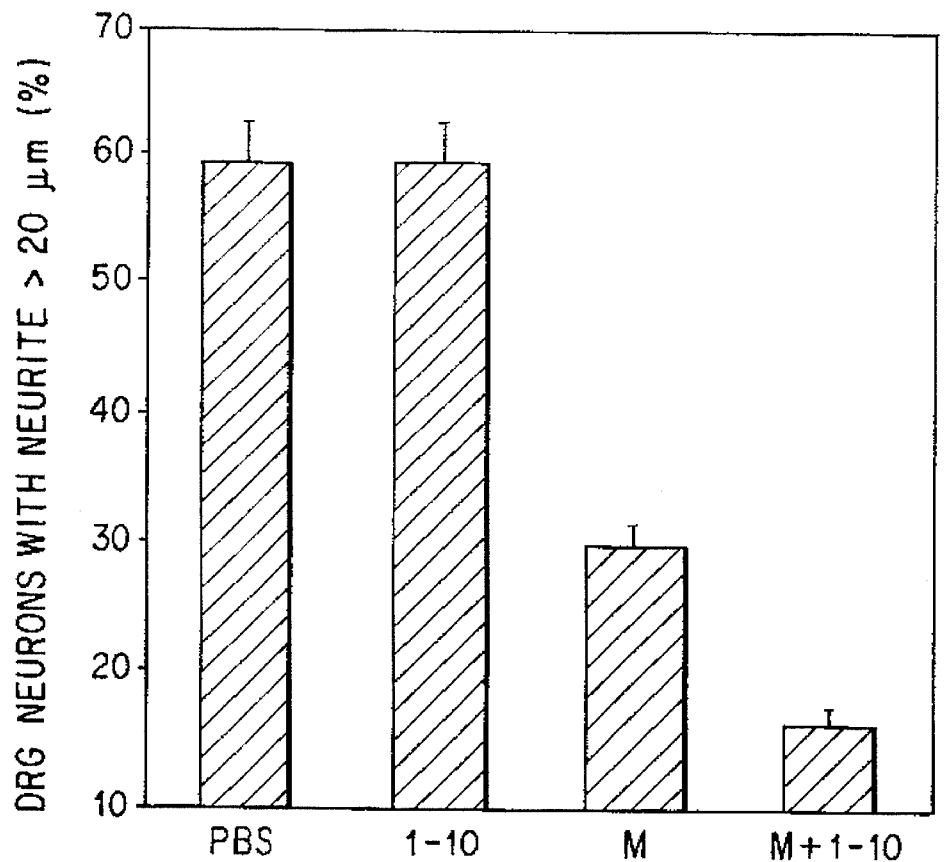

Myelin proteins solubilized by octylglucoside also cause growth cone collapse. This effect is also potentiated by the GAP-43 1–10 peptide. Low doses of the GAP-43 1–10 peptide potentiate the inhibition of DRG neurite outgrowth by solubilized myelin proteins (FIG. 1C). The potentiation of the response to BME by the GAP-43 1–10 peptide is blocked by 20 ng/ml PTX (FIG. 1D), showing that, like the collapse induced by higher BME concentrations, a PTX-sensitive G protein is involved. These data suggest that the GAP-43 peptide promotes collapse by amplifying G protein sensitivity to inhibitory ligands.

Figure 2A:
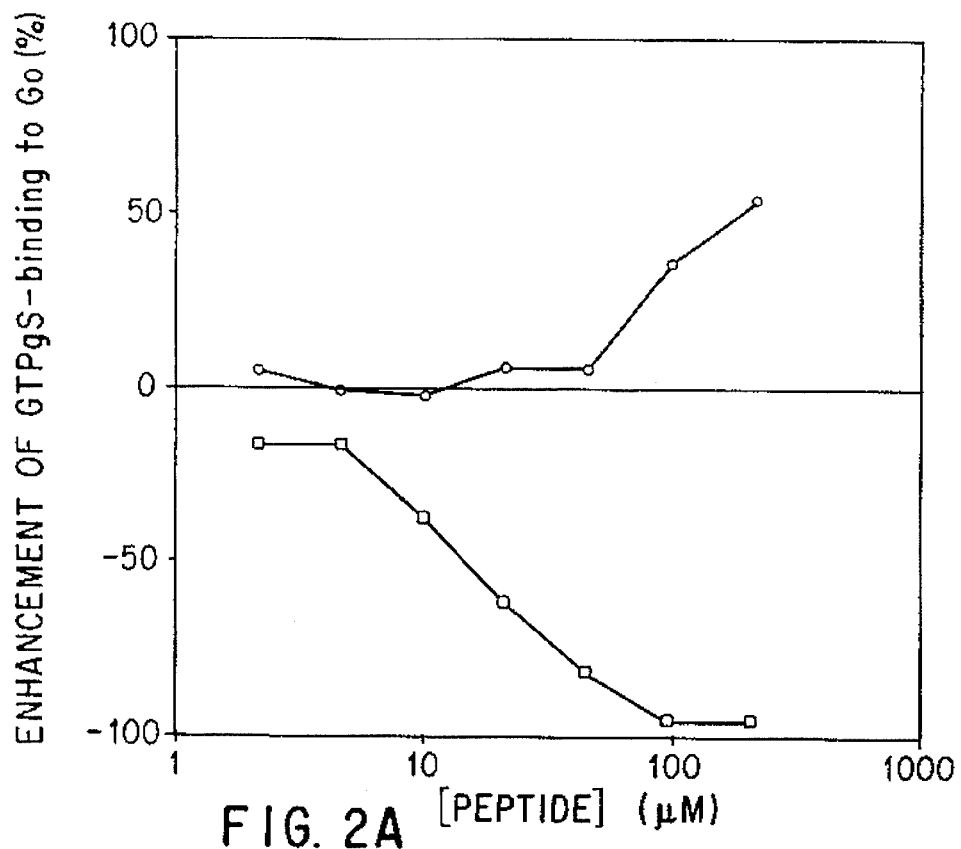
FIG. 2(A) and (B): Effect of peptide modification upon GTP$_\gamma$S binding to G$_o$. Oxidation of the GAP-43 1–10 N-terminus (MLCCMRRTKQ [SEQ ID NO: 1]; square) causes a dose-dependent inhibition, whereas the control peptide (circle) causes a dose-dependent simulation.
Figure 2B:
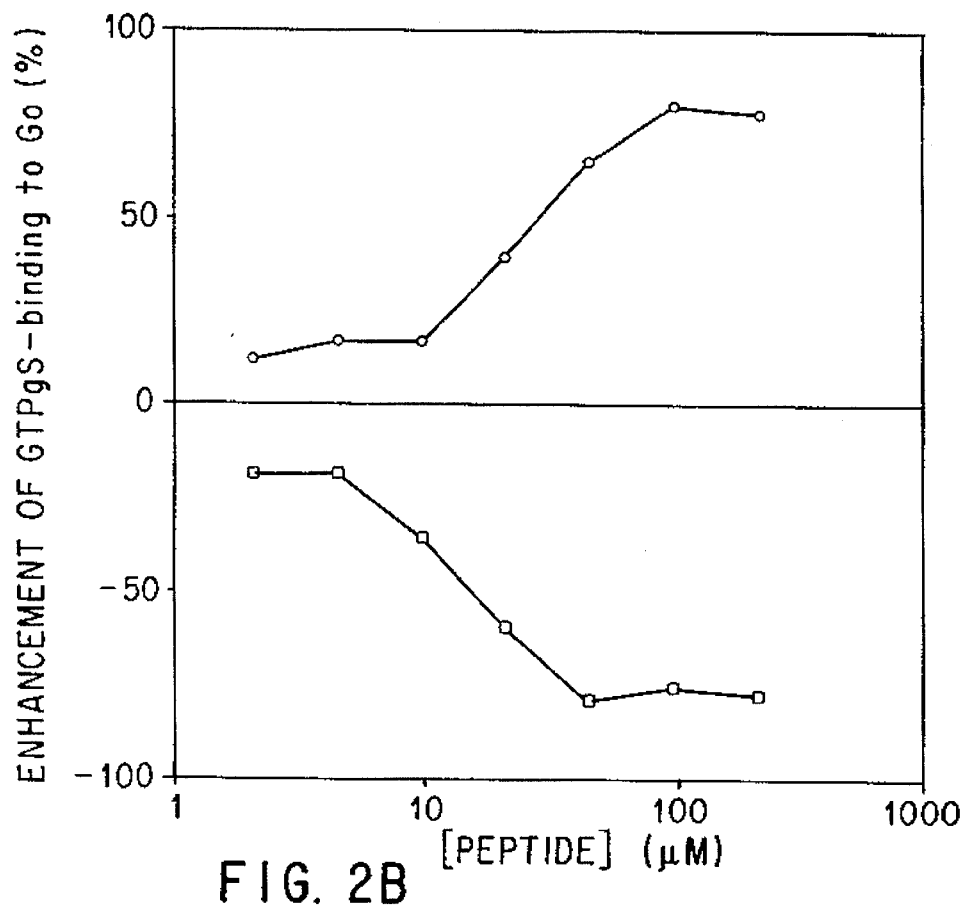

The above data posed the question of whether similar peptides could be designed that would interfere with G protein signaling, thereby inhibiting growth cone collapse. It had previously been found that the amino terminal decapeptide of GAP-43, if stored without dithiothreitol (DTT), acquires the ability to inhibit G$_o$ (S. M. Strittmatter et al., *J. Biol. Chem.* 266:22465 (1991)), suggesting that oxidation or other modification of the cysteines could change the activity of the peptide. As shown in FIGS. 2A and B, oxidation of the peptide by performic acid renders it inhibitory for G$_o$. The sensitivity to oxidation presumably explains why the GAP-43 1–10 peptide stored without DTT is inhibitory to G$_o$, whereas that stored with DTT is stimulatory (Y. Sudo et al., *EMBO J.* 11:2095 (1992)). It was felt that oxidation might be insufficiently stable for the examination of this peptide's bioactivity, since the interior of the cell is a reducing environment (C. Hwang et al., *Science* 257:1496 (1992)). Therefore, several peptides with different amino acids substituted for the two cysteines were synthesized. The preparation of these peptides, or their functional derivatives, can be achieved by employing well known techniques in the field of peptide chemistry. For example, the Merrifield procedure for solid-state peptide synthesis can be used (B. Gutte and R. B. Merrifield, *J. Biol. Chem.* 246(6):1922 (1971)). This procedure involves attaching a t-Butoxycarbonyl protected amino acid to a solid polystyrene resin, removal of the amino protecting group, and forming a peptide linkage between the resin bound amino acid and a second protected amino acid via a carbodiimide mediated condensation. This procedure is repeated with the appropriate amino acids until the desired peptide has been synthesized. Other techniques and reagents for the preparation of peptides are well known in the art, and are set forth, for example, in Bodanszky, M., et al., *The Practice of Peptide Synthesis*, Springer-Verlag, publisher, New York, N.Y. (1984), and in Bodanszky, M., *The Principles of Peptide Synthesis*, Springer-Verlag, publisher, New York, N.Y. (1984).

Figure 3A:
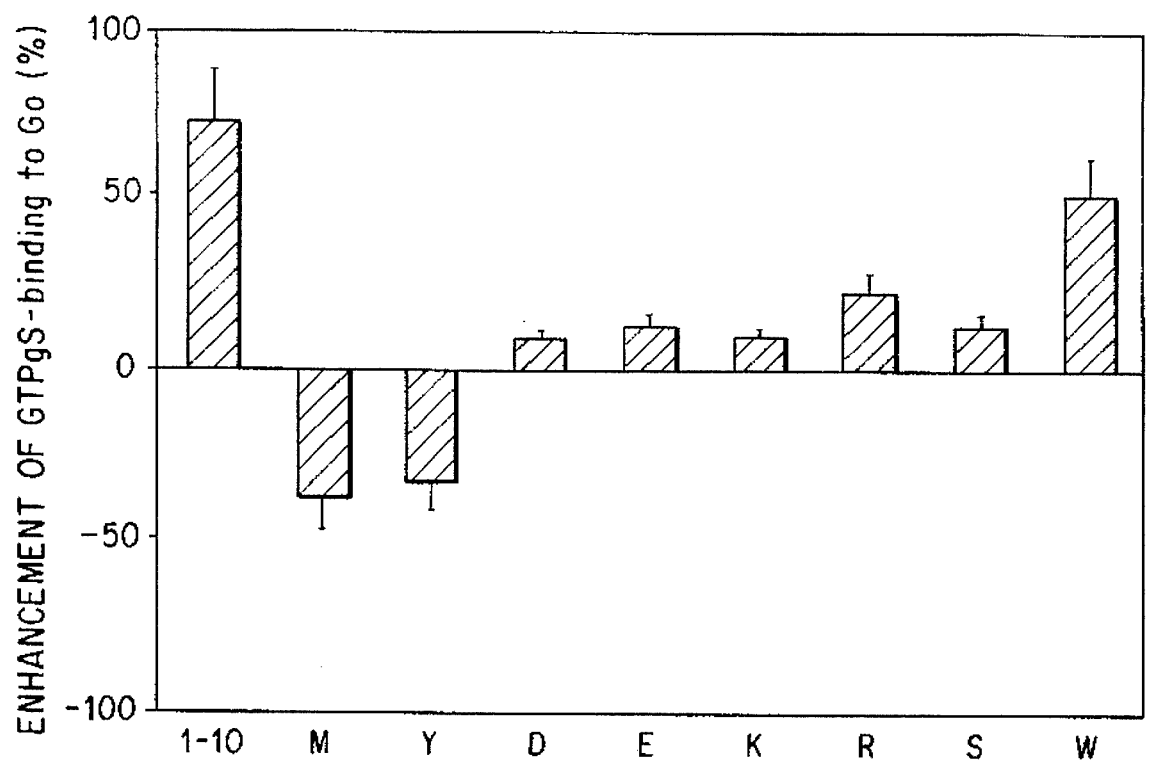
FIG. 3(A): The effect of mutant decapeptides upon GTP$_\gamma$S binding to G$_o$. In each case the single letter indicates the amino acid substituted for Cys$^3$ and Cys$^4$. The concentration of each peptide was 250 μM. The activity of GTP$_\gamma$S-binding to G$_o$ protein without peptides is shown as 100%. The sequence of native N-terminus decapeptide of rat GAP-43 (1–10 peptide) is MLCCMRRTKQ [SEQ ID NO: 1]. Both cysteine residues at positions 3 and 4 in the native 1–10 peptide were replaced with methionine (M) [SEQ ID NO: 2], tyrosine (Y) [SEQ ID NO: 3], aspartate (D) [SEQ ID NO: 4], glutamate (E) [SEQ ID NO: 5], lysine (K) [SEQ ID NO: 6], arginine (R) [SEQ ID NO: 7], serine (S) [SEQ ID NO: 8], and tryptophan (W) [SEQ ID NO: 9]. The values shown are the means ±S.E.M. for three separate experiments.
Figure 3B:
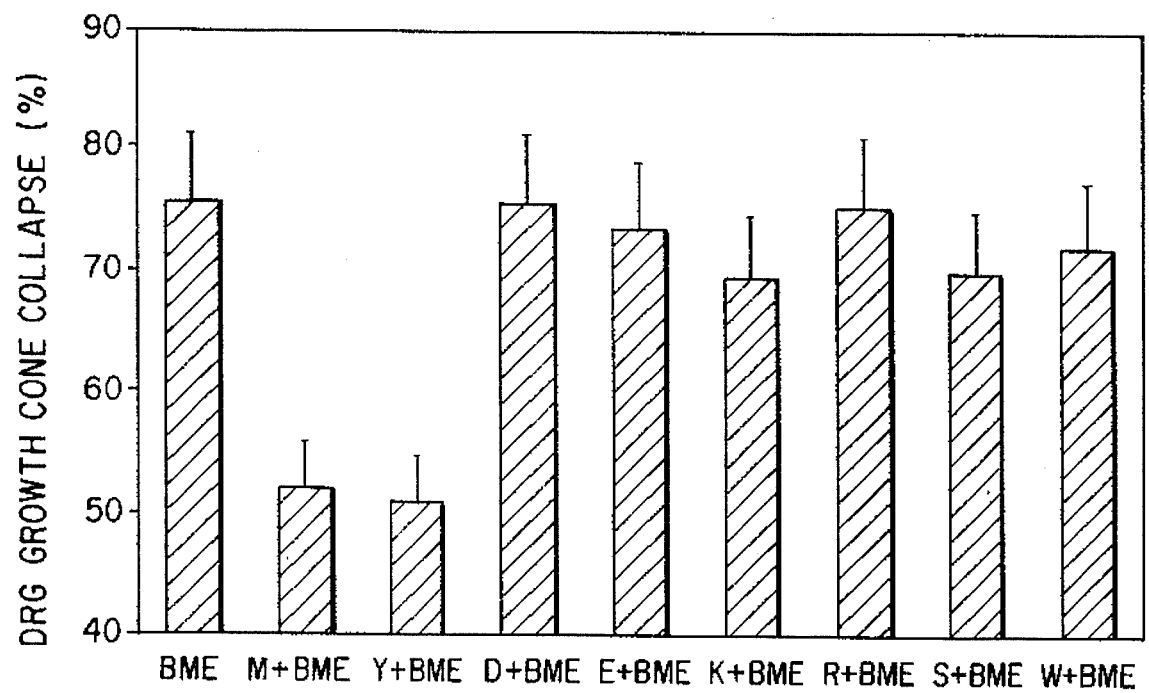
FIG. 3(B): Brain membrane-induced growth cone collapse of DRG neurons is inhibited by two mutant peptides. The concentration of BME was 0.15 mg protein/ml. One hour prior to the addition of BME to DRG culture medium, each mutant peptide was added at a concentration of $10^{-4}$M. Note that peptide-M and peptide-Y, which attenuate GTP$_\gamma$S binding to G$_o$, also attenuate the effect of BME. The values shown are the means ±S.E.M. for four separate experiments.
Figure 3C:
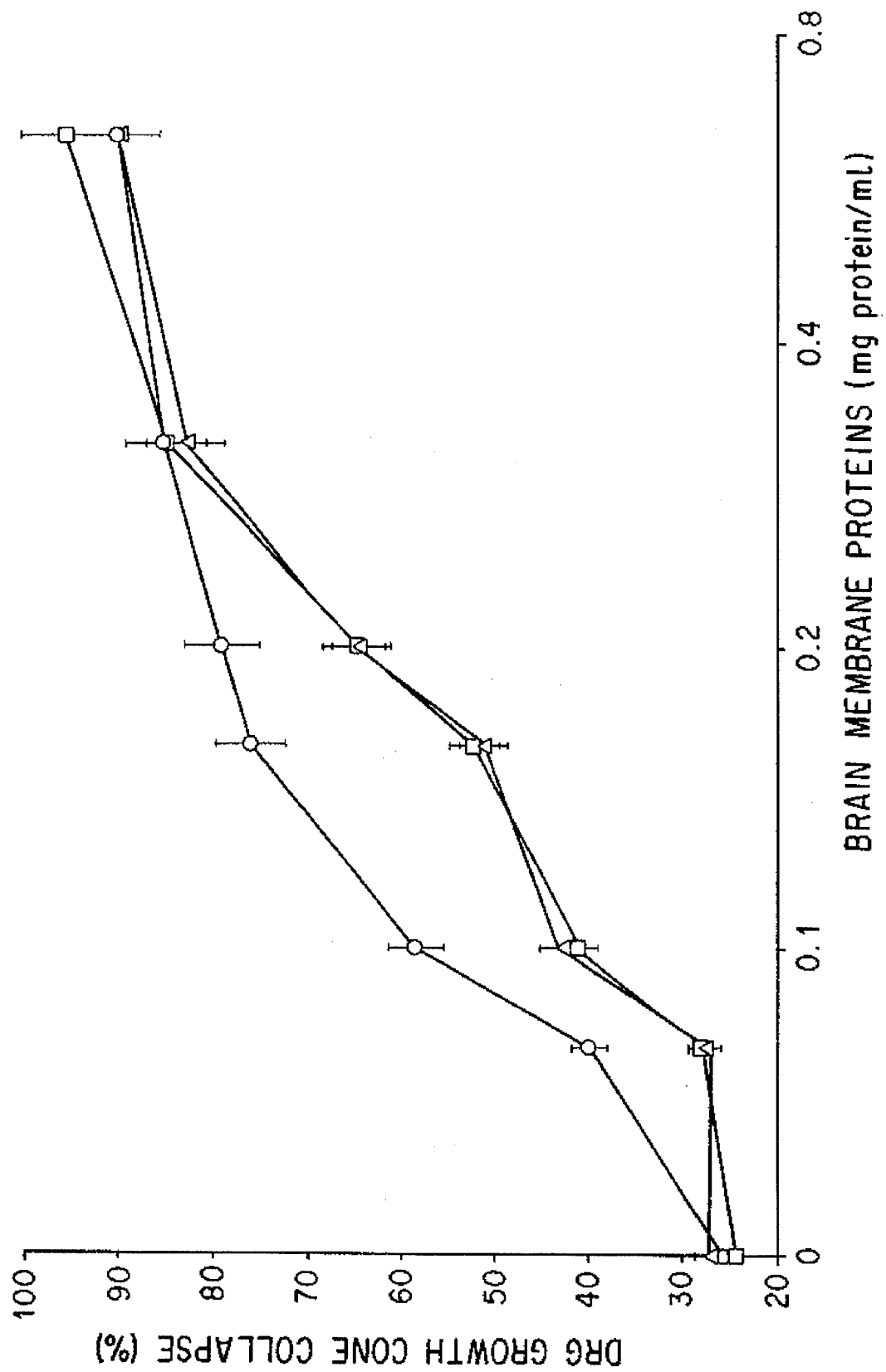
FIG. 3(C): Dose-response curves of BME vs. DRG growth cone collapse in the absence of peptides (circle) and in the presence of $10^{-4}$M peptide-M (square) and $10^{-4}$M peptide-Y (triangle). Solutions of peptides were prepared in PBS, 1 mM DTT just prior to use. The values shown are the means ±S.E.M. for four separate experiments.

As shown in FIG. 3A, most modifications render the peptide inactive with regard to G protein stimulation, but two, the substitution with tyrosine (Y) or with methionine (M) result in the GAP-43 1–10 peptide becoming an antagonist of G protein stimulation. It was examined whether these peptides could affect the sensitivity of growth cones to brain membrane extracts. Using concentrations of BME that cause maximal levels of collapse, the addition of either the tyrosine-substituted (Y) or methionine-substituted (M) peptide reduced the degree of growth cone collapse to baseline levels (FIG. 3B). The other peptides tested were not able to bring collapse to baseline levels. The response to increasing concentrations of brain membrane extracts in the presence of the 1–10 peptide, or the M or Y substituted peptides, at doses which do not have any evident effect by themselves, is shown in FIG. 3C. This data shows that the dose response curve is shifted to the right, so that in the presence of M or Y substituted peptides, about twice as much BME is needed to cause 50% collapse.

The present invention has therapeutic utility in the treatment of patients who have neurological trauma or disease where the promotion of neuron growth is desired. The specific preclinical and clinical therapeutic use of the present invention in the treatment of the aforementioned neurological disorders will be best accomplished by those of skill, employing the accepted principles of diagnosis and treatment. Such principles are known in the art, and are set forth, for example, in Petersdorf, R. G., et al., eds., *Harrison's Principles of Internal Medicine*, 10th ed., McGraw-Hill, publisher, New York, N.Y. (1983).

The peptides of the present invention, or their functional derivatives, are well suited for the preparation of pharmaceutical compositions. The pharmaceutical compositions of the invention may be administered to any animal which may experience the beneficial effects of the compounds of the invention. Foremost among such animals are humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the desired effect.

In addition to the pharmacologically active compounds, the new pharmaceutical preparations may contain suitable pharmaceutically acceptable carriers comprising excipients and auxiliaries which facilitate processing of the active compounds into preparations which can be used therapeutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.001 to approximately 99%, preferably from about 0.01 to about 95% of active compound(s), together with the excipient.

The dose ranges for the administration of the compositions of the present invention are those large enough to produce the desired effect. The doses should not be so large as to cause adverse side effects, such as unwanted cross reactions and/or anaphylactic reactions. Generally, the dosage will vary with age, condition, sex and the extent of the neurological disorder in the patient.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired, to obtain tablets or dragee cores.

Suitable excipients are fillers such as saccharides, for example, lactose or sucrose, mannitol or sorbitol, cellulose preparations, and/or calcium phosphates, for example, tricalcium phosphate or calcium hydrogen phosphate, as well as binders such as starch paste, using, for example, maize starch, wheat starch, rice starch, potato starch, gelatine, methylcellulose, carboxymethylcellulose, and/or polyvinylpyrrolidone. If desired, disintegrating agents may be added such as the above-mentioned starches and also carboxymethyl-starch, crosslinked polyvinylpyrrolidone, agar, or alginic acid or a salt thereof, such as sodium alginate. Auxiliaries are, above all, flow regulating agents and lubricants, for example, silica, talc, stearic acid or salts thereof, such as magnesium stearate or calcium stearate, and/or polyethylene glycol.

Suitable formulations for parenteral administrations include aqueous solutions of the active peptides in water-soluble form, for example, water-soluble salts. In addition, suspensions of the active compounds as appropriate oily injection suspensions may be administered. Suitable lipophilic solvents or vehicles including fatty oil, for example, sesame oil or synthetic fatty acid esters, for example, ethyl oleate or triglycerides. Aqueous injection suspensions may contain substances which increase the viscosity of the suspension, including, for example, sodium carboxymethylcellulose, sorbitol, and/or dextran. Optionally, the suspension may also contain stabilizers.

Any terms which are used herein and are not specifically defined in this application are used as they would be by one of ordinary skill in the art(s) to which the invention pertains.

The Examples which follow are for illustrative purposes only and are not intended to limit the scope of the invention.

EXAMPLE 1

Preparation of the Tyrosine and Methionine Substituted GAP-43 1–10 Peptides

Materials and Methods
A. Synthesis of Methionine Substituted GAP43 1–10 Peptide ([3M, 4M] GAP43 (1–10)):

Chloromethylated polystyrene vinylbenzene resin (crosslinked with 1% divinylbenzene, containing 0.66 mmol of chloride per g of the resin) of 100 to 200 mesh was employed. Upon synthesis of [3M, 4M]GAP43 (1–10), 5.00 g of Boc—Gln—OH was dissolved in a mixture of 20 ml of ethyl alcohol and 18 ml of water, and the pH adjusted to 7.0 with a 20% cesium carbonate solution. The solution was concentrated in vacuo and then desiccated. 100 ml of DMF and 20.5 g of the chloromethylated resin were added to the residue and the mixture stirred for 20 hours at 50° C. to allow esterification. The resulting Boc—Gln—O—resin was filtered, washed sequentially with 90% DMF and ethyl alcohol, and then desiccated. Product yield=21.24 g.

Ten grams of the Boc—Gln—O—resin was charged in a solid phase synthesis reactor. Following the procedure described in Schedule A, Boc—Lys(ClZ)—OH, Boc—Thr(Bzl)—OH, Boc—Arg(Tos)—OH, Boc—Arg(Tos)—OH and Boc—Met—OH were successively coupled to the resin to yield 12.85 g of the GAP43(5–10) peptide resin. 3.00 g of the GAP43(5–10) resin was then sequentially coupled with Boc—Met—OH, Boc—Met—OH, Boc—Leu—OH and Boc—Met—OH. This procedure yielded 3.19 g of the [3M, 4M] GAP43(1–10) peptide.

3.0 ml of anisole, 0.5 ml of ethylmethyl sulfide and 20 ml of anhydrous hydrogen fluoride was added to 1.99 g of the [3M 4M]GAP43(1–10) peptide resin. The mixture was reacted at −20° C. for 60 minutes and then at 0° C. for 60 minutes. The reaction mixture was concentrated in vacuo, and 250 ml of diethyl ether was added to the residue. The slurry was stirred for 30 minutes, filtered and washed with 60 ml of diethyl ether. To the residue was added 50 ml of 2N aqueous acetic acid. After stirring for 2 hours, the resin was filtered off and washed with 50 ml of 2N aqueous acetic acid. The filtrate was lyophilized to yield 231 mg of the crude peptide.

100 mg of the crude peptide was dissolved in 50 ml of 1N aqueous acetic acid, and the solution applied to a reverse phase YMC-SH-343-5(S-5) ODS column (20 mm×250 mm) previously equilibrated with an 0.1% TFA solution. The column was washed with aqueous 0.1% TFA, and the peptide eluted with a linear gradient of aqueous accetonitrile (0 to approximately 15% acetonitrile in 360 minutes), at a flow rate of 4.0 ml/min. The eluent was monitored at A220 nm and the fractions containing the desired product were collected and lyophilized to yield 42.6 mg of [3M, 4M]GAP43(1–10).

The obtained [3M, 4M]GAP43(1–10) was applied to a reverse phase YMC-AM303(S-5)-ODS column (4.6 mm×250 mm) and eluted employing a linear gradient of 10–40% aqueous acetonitrile containing 0.1% TFA (retention time, 21.1 minutes). The obtained peptide was analyzed for amino acid content.

Amino Acid Analysis

Hydrolysis:
6N HCl, 1% phenol, at 100° C. for 24 hours
Analysis method:
PICO-TAG (reverse phase-PTC amino acid) method
Result:
Gln: 1.03 (1)
Arg: 2.09 (2)
Thr: 1.06 (1)
Met: 4.47 (4)
*Leu: 1.00 (1)
Lys: 1.04 (1)

*Leu was used as a standard amino acid. The values in parentheses indicate calculated values.

Mass spectrum (FAB) [M+H]+: 1325.3

B. Synthesis of Tyrosine Substituted GAP-43 1–10 Peptide ([3Y, 4Y]GAP43 (1–10)):

10.82 g of the Boc—Gln—O—resin described above were charged in a solid phase synthesis reactor. Following the procedure described in Schedule A, Boc—Lys(ClZ)—OH, Boc—Thr(B1)—OH, Boc—Arg(Tos)—OH and Boc—Met—OH were successively coupled with the resin to yield 13.43 g of the GAP43(5–10) peptide resin. 3.30 g of this GAP43(5–10) resin was then sequentially coupled with Boc—Tyr(Cl2Bzl)—OH, Boc—Try(Cl2Bzl)—OH, Boc—Leu—OH and Boc—Met—OH, and 3.56 g of [3Y, 4Y]GAP43(1–10) peptide resin was obtained.

To 2.0 g of the [3Y, 4Y]GAP43(1–10) peptide resin was added 3.0 ml of anisole, 0.5 ml of ethylmethyl sulfide, and 20 ml of anhydrous hydrogen fluoride. The mixture was reacted at −20° C. for 60 minutes and then at 0° C. for 60 minutes. The reaction mixture was concentrated in vacuo, and 50 ml of diethyl ether added to the residue. The slurry was stirred for 60 minutes, filtered, and then washed with 60 ml of diethyl ether. To the residue was added 50 ml of 2N aqueous acetic acid. After stirring for 2 hours, the resin was filtered off and washed with 50 ml of 2N aqueous acetic acid. The filtrate was lyophilized to yield 209 mg of crude peptide.

100 mg of the crude peptide was dissolved in 15 ml of aqueous 0.1% TFA and the solution applied to a reverse phase YMC-SH-363-5(S-5)ODS column (30 mm×250 mm) previously equilibrated with 0.1% TFA. The column was washed with aqueous 0.1% TFA, and the peptide eluted with a linear gradient of aqueous acetonitrile (0 to approximately 15% acetonitrile in 360 minutes), at a flow rate of 7.0 ml/min. The eluent was monitored at A220 nm, and the fractions containing the desired product were collected and lyophilized to yield 25.5 mg of [3Y, 4Y]GAP43(1–10).

The obtained [3Y, 4Y]GAP43(1–10) was applied to a reverse phase YMC-AM303(S-5)-ODS column (4.6 mm×250 mm) and eluted employing a linear gradient of 15–35% aqueous acetonitrile containing 0.1% TFA (retention time 14.9 minutes). The obtained peptide was analyzed for amino acid content.

Results

Amino Acid Analysis

Hydrolysis:
6N HCl, 1% phenol, at 110° C. for 24 hours
Analysis method:
PICO-TAG (reverse phase-PTC amino acid) method
Result:
Gln: 0.97 (1)
Arg: 1.86 (2)
Thr: 0.87 (1)
Met: 1.79 (2)
Tyr: 1.96 (2)
*Leu: 1.00 (1)
Lys: 1.01 (1)

*Leu was used as a standard amino acid. The values in parentheses indicate calculated values.

Mass spectrum (FAB) [M+H]+: 1389.3

| Steps Schedule A | Time (min.) × Treatment Times |
|---|---|
| 1. Washing with methylene chloride, 60 ml | 2 × 3 |
| 2. Deprotection with 50% TFA, 5% ethanediol, 45% methylene chloride (V/V), 60 ml | 3 × 1<br>20 × 1 |
| 3. Washing with methylene chloride, 60 ml | 2 × 2 |
| 4. Washing with methanol, 60 ml | 2 × 2 |
| 5. Neutralization with 10% triethylamine, 90% methylene chloride (VV), 60 ml | 1 × 1 |
| 6. Washing with methanol, 60 ml | 2 × 1 |
| 7. Neutralization with 10% triethylamine, 90% methylene chloride (V/V), 60 ml | 1 × 1 |
| 8. Washing with methanol, 60 ml | 2 × 2 |
| 9. Washing with methylene chloride, 60 ml | 2 × 2 |
| 10. Coupling with various amino group-protected amino acids (6 mmols), additive (HOBt 50% DMF-50% methylene chloride (V/V), 30 ml<br>Solution of DCC (6 mmols) in methylene chloride, 12 ml | 5 × 1<br><br><br><br>120 × 1 |
| 11. Washing with 50% DMF, 50% methylene chloride (V/V), 60 ml | 2 × 2 |
| 12. Washing with methanol, 60 ml | 2 × 1 |
| 13. Neutralization with 10% triethylamine, 90% methylene chloride (V/V), 60 ml | 1 × 1 |
| 14. Washing with methanol, 60 ml | 2 × 2 |
| 15. Washing with methylene chloride, 60 ml | 2 × 2 |
| 16. Acetylation with 25% acetic anhydride, 75% methylene chloride (V/V), 60 ml | 15 × 1 |
| 17. Washing with methylene chloride, 60 ml | 2 × 2 |
| 18. Washing with methanol, 60 ml | 2 × 2 |

EXAMPLE 2

Effect of Brain Membrane Extracts on Dorsal Root Ganglion and Retinal Neuron Growth Cones in the Presence of GAP-43 1–10 Peptide Materials and Methods Chick DRGs from embryonic day 7 (E7) were explanted onto laminin-coated chamber slides in F12 medium with 10 ng/ml nerve growth factor and 10% fetal bovine serum. After 20 hours, peptide solutions or phosphate-buffered saline (PBS) in 1 mM DTT was added to the explants (225 µl) and the mixture incubated at 27° C. for one hour. BME, prepared following the procedure of J. A. Raper and J. P. Kapfhammer, *Neuron* 2:21 (1990), was added to the explants and incubated for 30 minutes. For each explant, all growth cones were scored as collapsed or fan-shaped (M. Igarashi et al., *Science* 259:77 (1993)).

In another series of experiments the GAP-43 1–10 peptide was added into the culture medium at $10^{-8}$M one hour prior to the addition of BME. After 30 minutes incubation with BME, the explant was fixed in glutaraldehyde and its growth cones were scored.

For culture of retina, chick E7 retina was cut into small pieces and explanted and assayed as described for DRG cultures (M. Igarashi et al., *Science* 259:77 (1993)).

Results

The collapse of dorsal rat ganglion growth cones induced by brain membrane extracts (BME) was increased approximately two-fold by pretreatment with the GAP-43 1–10 peptide (FIG. 1A). The sensitivity of retinal growth cones to BME was also significantly increased (FIG. 1B).

EXAMPLE 3

Effect of Solubilized Myelin on Neurite Outgrowth in the Presence of GAP-43 1–10 Peptide Materials and Methods For assays of effects upon neurite growth, chick DRGs from E7 were trypsinized at 37° C. for 30 minutes and triturated. The dissociated cells were first plated on fibronectin-coated dishes for two hours to remove non-neuronal cells (P. C. Letourneau et al., *J. Neurobiol.* 22:707 (1992)), and then plated onto liminin-coated chamber slides in the presence of GAP-43 1–10 peptide or PBS buffer. One hour later, myelin proteins, solubilized by octylglucoside (M) and dialyzed against F12 medium, were added to the dissociated DRG neurons (M. Igarashi et al., *Science* 259:77 (1993)). After 6 hours of culture, cells were fixed by 1% glutaraldehyde in PBS, and the fraction of neurons with a process longer than 20 μm was determined.

Results

The results shown in FIG. 1C indicate that the GAP-43 1–10 peptide alone does not inhibit neurite outgrowth. The results also indicate that M alone reduces the percentage of neurons with neurite outgrowths exceeding 20 μM by 50% as compared to controls, and this inhibition is potentiated by pretreating the neurons with $10^{-9}$M GAP-43 1–10 peptide.

EXAMPLE 4

Effect of Pertussis Toxin on GAP-43 1–10 Peptide

Materials and Methods

Neurons were pretreated with pertussis toxin (PTX) at concentrations which do not inhibit the collapse of growth cones induced by BME. After exposing the PTX treated neurons to BME and the GAP-43 1–10, the amount of growth cone collapse was measured.

Results

Figure 1D:
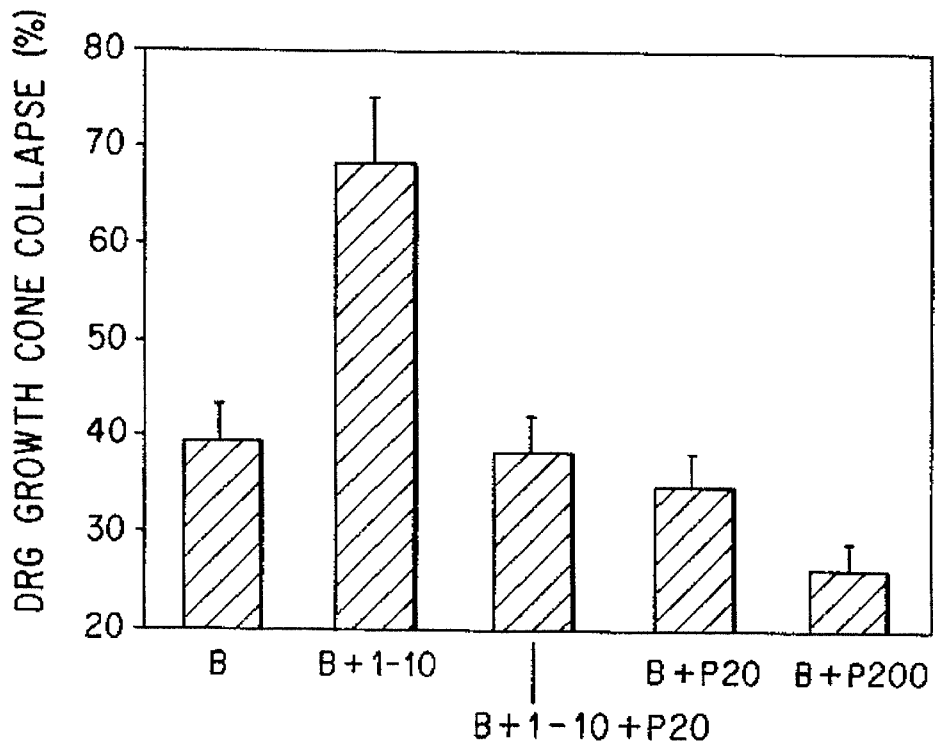

The data presented in FIG. 1D demonstrate that pertussis toxin at a concentration of 20 ng/ml blocks the GAP-43 1–10 potentiation of BME induced growth cone collapse.

EXAMPLE 5

Effect of Peptide Oxidation on GTP$_\gamma$S Binding to $G_o$

Materials and Methods

The GAP-43 1–10 peptide was oxidized using performic acid according to the procedures of A. Roher et al., *Proc. Natl. Acad. Sci. USA* 83:2662 (1986). Briefly, 10 mM peptide was incubated with formic acid solution containing 3% $H_2O_2$ at 25° C. for one hour. The activation state of $G_o$ was determined in a nitrocellulose filtration assay as described by S. M. Strittmatter et al., *Proc. Natl. Acad. Sci. USA* 90:5327 (1993).

Results

Oxidation of the GAP-43 1–10 N terminus causes a dose-dependent inhibition of GTP$_\gamma$S binding to $G_o$, whereas the control GAP-43 1–10 peptide causes a dose-dependent stimulation of GTP$_\gamma$S binding to $G_o$ in the same concentration range. (FIGS. 2A and B; control peptide circle, oxidized peptide square).

EXAMPLE 6

The Effect of Mutant Decapeptides On GTP$_\gamma$S Binding to $G_o$

Materials and Methods

All GAP-43 peptides were chemically synthesized and their composition verified by amino acid analysis and mass spectrometry.

Both cysteine residues at positions 3 and 4 in the native GAP-43 1–10 peptide were replaced with methionine, tyrosine, aspartate, glutamate, lysine, arginine, serine, and tryptophan. These mutant peptides were tested for their ability to influence GTP$_\gamma$S binding to $G_o$.

Results

As shown in FIG. 3A, most substitutions at the 3 and 4 positions result in a peptide less active in stimulating GTP$_\gamma$S binding to $G_o$. However, substitutions at these positions with either methionine or tyrosine result in a peptide which inhibits GTP$_\gamma$S binding to $G_o$.

EXAMPLE 7

Effect of the Methionine and Tyrosine Substituted GAP-43 1–10 Peptides on Brain Membrane Induced Growth Cone Collapse Materials and Methods The procedure described in Example 2 was followed with the exception that one hour prior to the addition of BME (0.15 mg protein/ml) to the DRG culture medium, either the methionine or tyrosine mutant peptide was introduced at a concentration of $10^{-4}$M.

Results

Both the methionine and tyrosine substituted peptides inhibit the growth cone collapse induced by BME approximately 30%. The other peptide mutants tested had no significant effect on BME induced collapse.

All publications mentioned in this specification are indicative of the level of skill of one in the art to which this invention pertains. All publications are hereby incorporated by reference to the same extent as if each individual publication was specifically and individually indicated to be incorporated by reference.

What is claimed is:

1. A decapeptide having the formula:

Met—Leu—X—X—Met—Arg—Arg—Thr.—Lys—Gln wherein X—X is Tyr—Tyr [SEQ ID NO: 3] or Met—Met [SEQ ID NO: 2].

2. The decapeptide of claim 1, wherein X—X is Tyr—Tyr [SEQ ID NO: 3].

3. The decapeptide of claim 1, wherein X—X is Met—Met [SEQ ID NO: 2].

4. A composition comprising the decapeptide of claims 1, 2 or 3, together with a pharmaceutically acceptable carrier.

* * * * *